(12) United States Patent
Solbakken et al.

(10) Patent No.: US 7,875,701 B2
(45) Date of Patent: Jan. 25, 2011

(54) DIAGNOSTIC COMPOUNDS

(75) Inventors: Magne Solbakken, Oslo (NO); Bente Arbo, Oslo (NO); Alan Cuthbertson, Oslo (NO); Alexander Gibson, Little Chalfont (GB)

(73) Assignee: GE Healthcare AS, Oslo (NO)

( * ) Notice: Subject to any disclaimer, the term of this patent is extended or adjusted under 35 U.S.C. 154(b) by 987 days.

(21) Appl. No.: 11/575,163

(22) PCT Filed: Sep. 14, 2005

(86) PCT No.: PCT/IB2005/002727
§ 371 (c)(1), (2), (4) Date: Mar. 13, 2007

(87) PCT Pub. No.: WO2006/030291
PCT Pub. Date: Mar. 23, 2006

(65) Prior Publication Data
US 2008/0095701 A1    Apr. 24, 2008

(30) Foreign Application Priority Data
Sep. 14, 2004    (GB) ................................ 0420344.4

(51) Int. Cl.
*A61K 38/04*    (2006.01)
(52) U.S. Cl. ..................................... 530/329; 424/1.89
(58) Field of Classification Search ................. 530/300, 530/317, 329
See application file for complete search history.

(56) References Cited

FOREIGN PATENT DOCUMENTS

| WO | 03/006491 | 1/2003 |
|---|---|---|
| WO | 03/080544 | 10/2003 |
| WO | 2004/080492 | 9/2004 |
| WO | 2005/012335 | 2/2005 |

OTHER PUBLICATIONS

PCT/IB2005/002727 Int'l Search Report and Written Opinion dated Apr. 5, 2007.
Poethko T, et.al. "Two-step methodology for high-yield routine radiohalogenation of peptides: 18F-labeled RGD and octreotide analogs" Journal of Nuclear Medicine, Society of Nuclear Medicine, Reston ,VA, US, vol. 45, No. 5, May 2004, pp. 892-902.

*Primary Examiner*—Michael G Hartley
*Assistant Examiner*—Jagadishwar R Samala
(74) *Attorney, Agent, or Firm*—Craig Bohlken

(57) ABSTRACT

The invention relates to conjugates of formula (III) or (IIIa), or a salt thereof, their use as radiopharmaceuticals, processes for their preparation, and synthetic intermediates used in such processes.

2 Claims, No Drawings

DIAGNOSTIC COMPOUNDS

This application is a filing under 35 U.S.C. 371 of international application number PCT/IB2005/002727, filed Sep. 14, 2005, which claims priority to application number 0420344.4 filed Sep. 14, 2004, in Great Britain the entire disclosure of which is hereby incorporated by reference.

The present invention relates to new peptide-based compounds and their use for diagnostic imaging using positron emission tomography (PET). More specifically the invention relates to the use of such peptide-based compounds as targeting vectors that bind to receptors associated with angiogenesis, in particular integrin receptors, for example, the αvβ3 integrin receptor. Such compounds may thus be used for diagnosis or therapy of, for example, malignant diseases, heart diseases, endometriosis, inflammation-related diseases, rheumatoid arthritis and Kaposi's sarcoma. It further relates to methods and reagents for production of such peptide-based compounds.

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes.

The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimetre size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO 03/006491 describes peptide-based compounds which target integrin receptors associated with angiogenesis. However, there exists a need for further such peptide-based compounds having utility for diagnostic imaging techniques such as PET. Co-pending International application PCT/GB2004/001052 describes methods suitable for labelling biologically active vectors with $^{18}$F. But there is still a need for peptide-based compounds which may be prepared rapidly and efficiently and yet still have the desirable biological activity.

In a first aspect, the present invention provides a method for radiofluorination comprising reaction of a compound of formula (I):

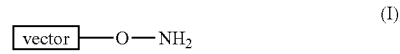

(I)

wherein the vector comprises the fragment:

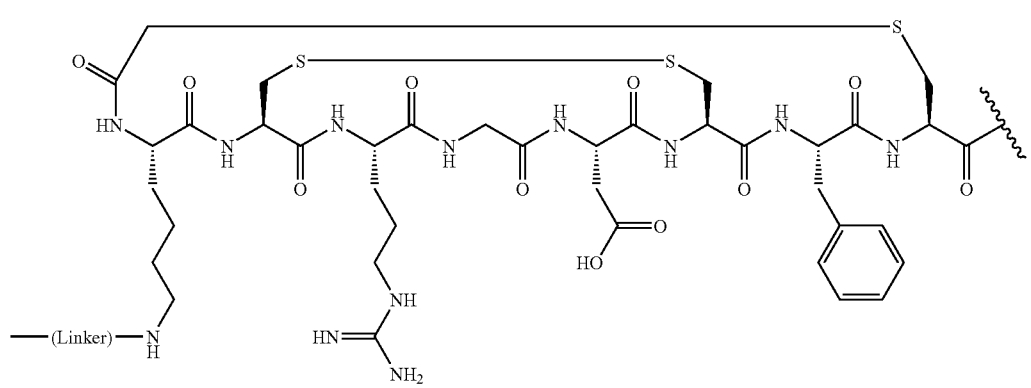

with a compound of formula (II):

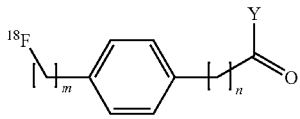
(II)

wherein:

n is an integer of 0 to 20;

m is an integer of 0 to 10;

Y is hydrogen, $C_{1-6}$alkyl (such as methyl), or phenyl to give a compound of formula (III):

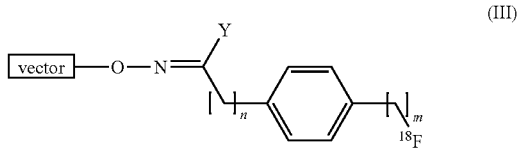
(III)

wherein m, n, and Y are defined as for the compound of formula (II) and the vector is as defined for the compound of formula (I).

This reaction may be effected in a suitable solvent, for example, in an aqueous buffer in the pH range 1 to 11, suitably 2 to 11, more suitably 2 to 6, and at a non-extreme temperature of from 5 to 100° C., suitably 20 to 70° C., preferably at ambient temperature.

In one particular aspect, the vector in formula (I) or (III) is of formula (A):

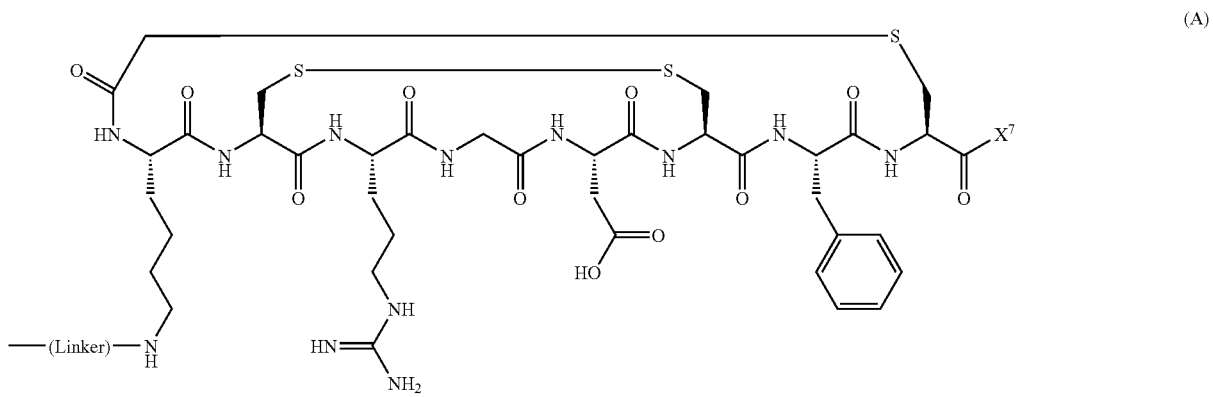
(A)

wherein $X^7$ is either —$NH_2$ or

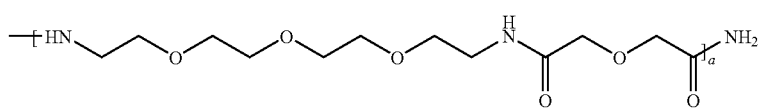

wherein a is an integer of from 1 to 10, preferably a is 1.

The Linker forming part of the vector in the compound of formula (I) is chosen to provide good in vivo pharmacokinetics, such as favourable excretion characteristics in the resultant conjugate of formula (III). The use of linker groups with different lipophilicities and or charge can significantly change the in vivo pharmacokinetics of the peptide to suit the diagnostic need. For example, where it is desirable for a conjugate of formula (III) to be cleared from the body by renal excretion, a hydrophilic linker is used, and where it is desirable for clearance to be by hepatobiliary excretion a hydrophobic linker is used. Linkers including a polyethylene glycol moiety have been found to slow blood clearance which is desirable in some circumstances.

The Linker forming part of the vector in the compound of formula (I) is a $C_{1-60}$ hydrocarbyl group, suitably a $C_{1-30}$ hydrocarbyl group, optionally including 1 to 30 heteroatoms, suitably 1 to 10 heteroatoms such as oxygen or nitrogen. Suitable Linker groups include alkyl, alkenyl, alkynyl chains, aromatic, polyaromatic, and heteroaromatic rings, and polymers comprising ethyleneglycol, amino acid, or carbohydrate subunits. Preferably, the Linker forming part of the vector in the compound of formula (I) comprises a polyethylene glycol subunit, most preferably the Linker is of formula B:

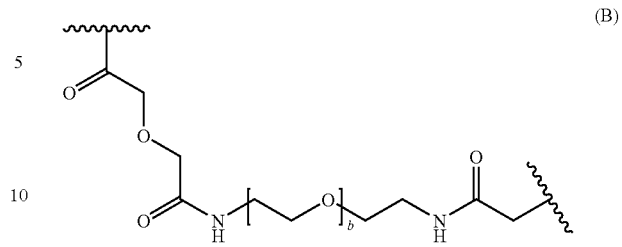

wherein b is an integer of from 2 to 20, and is preferably 3 to 10, most preferably 5.

The term "hydrocarbyl group" means an organic substituent consisting of carbon and hydrogen, such groups may include saturated, unsaturated, or aromatic portions.

Accordingly, preferred compounds of formula (I) are those of formula (Ia):

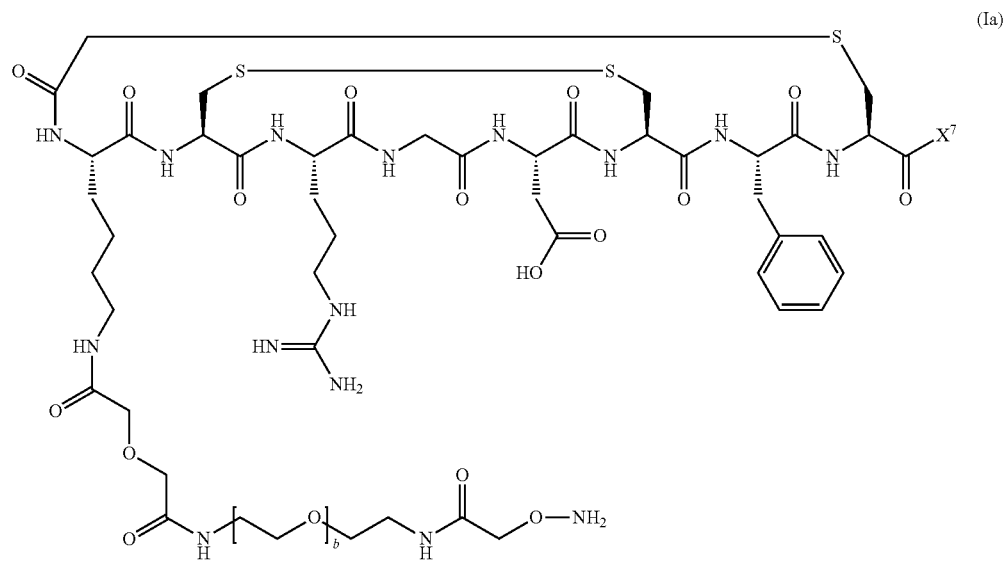

wherein $X^7$ is either —$NH_2$ or

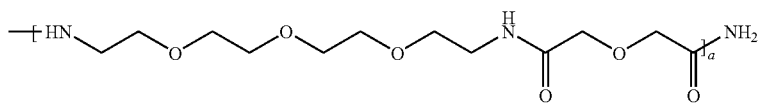

wherein a is an integer of from 1 to 10, preferably a is 1 and b is an integer of from 2 to 20 and is preferably 3 to 10, most preferably 5.
m Preferred compounds of formula (II) are those where m is 0, n is 0, and Y is hydrogen.

Compounds of formula (I) and (III) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the aminoxy group in a compound of formula (I) may be achieved by formation of a stable amide bond formed by reaction of a peptide amine function with an activated acid and introduced either during or following the peptide synthesis.

In another aspect, the present invention provides compounds of formula (I) and (Ia) as defined above having use as reagents useful for the production of radiolabelled peptide-based compounds.

In a further aspect the present invention provides radiolabelled conjugates of formula (III) or a salt thereof, as defined above. Preferred compounds of formula (III) are those of formula (IIIa):

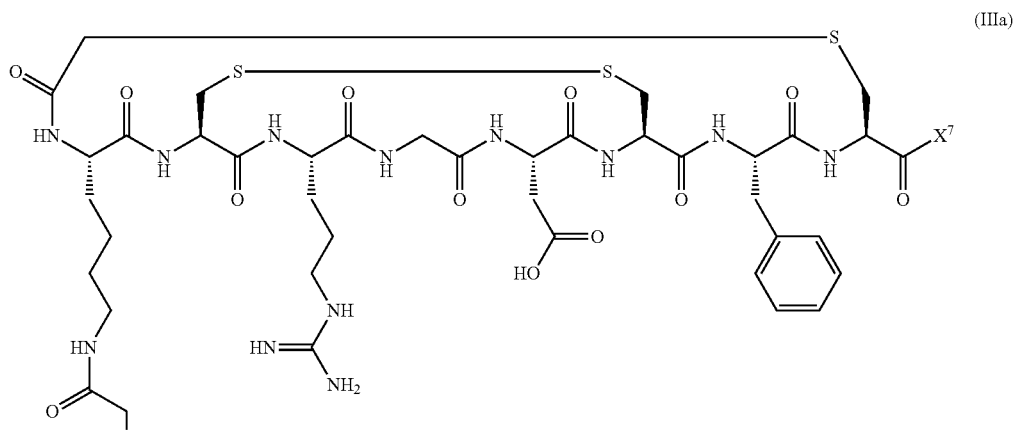

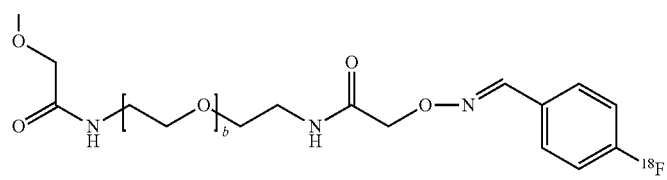

or a salt thereof, wherein $X^7$ is either —$NH_2$ or

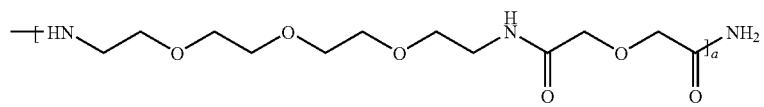

wherein a is an integer of from 1 to 10, preferably a is 1 and b is an integer of from 2 to 20 and is preferably 3 to 10, most preferably 5.

One particularly preferred compound of formula (III) is:

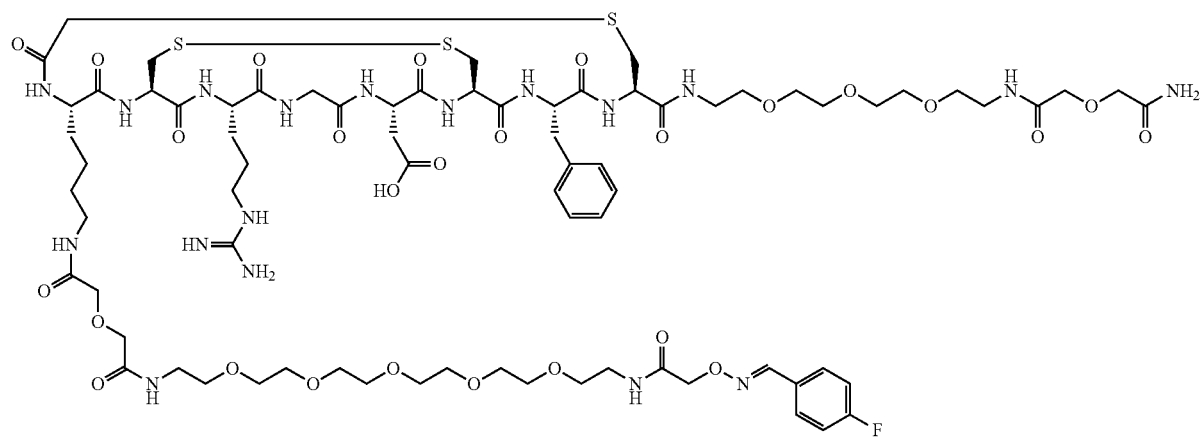

Suitable salts of the compounds of formula (III) and (IIIa) include pharmaceutically acceptable acid additions salts such as those formed from hydrochloric, hydrobromic, sulphuric, citric, tartaric, phosphoric, lactic, pyruvic, acetic, trifluoroacetic, succinic, oxaxlic, fumaric, maleic, oxalacetic, methanesulphonic, ethanesulphonic, p-toluenesulphonic, benzenesulphonic, and isoethionic acids.

Compounds of formula (II) may be prepared from the corresponding precursors of formula (IV):

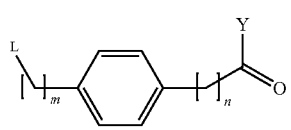

or a protected derivative thereof, wherein L is a leaving group preferably when m≧1, L is p-toluenesulphonate, trifluoromethanesulphonate, or methanesulphonate or a halide and when m is 0 L is p-trialkyl ammonium salt or p-nitro, and Y, m, and n are as described for the compound of formula (II); by reaction with cyclotron produced aqueous [$^{18}F$]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at ambient or at elevated temperature, for example up to 140° C. The aldehyde or ketone function of compounds of formula (II) can also be rapidly generated from their protected precursors such as acetals or ketals by simple acid treatment following fluorination.

As shown in the in vitro competition binding assay below, the compounds of formula (I) and (Ia) bind to receptors associated with angiogenesis. These compounds may thus be useful for treatment, in vivo diagnosis and imaging of diseases and conditions associated with angiogenesis.

The term "diseases and conditions associated with angiogenesis" includes those diseases and conditions referred to below. Reference is also made in this regard to WO 98/47541.

Diseases and conditions associated with angiogenesis include different forms of cancer and metastasis, for example, breast, skin, colorectal, pancreatic, prostate, lung or ovarian cancer.

Other diseases and conditions associated with angiogenesis are inflammation (for example, chronic inflammation), atherosclerosis, rheumatoid arthritis and gingivitis.

Further diseases and conditions associated with angiogenesis are arteriovenous alformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

The present invention also provides a radiopharmaceutical composition comprising an effective amount (e.g. an amount effective for use in in vivo PET imaging) of a compound of general formula (III) or (IIIa) or a salt thereof, as defined above; together with one or more pharmaceutically acceptable adjuvants, excipients or diluents.

A preferred embodiment of the invention relates to a compound of general formula (III) or (IIIa) or a salt thereof, as defined above, for use in medicine, particularly in the in vivo diagnosis or imaging, for example by PET, of a disease or condition associated with angiogenesis.

The radiolabelled conjugates of formula (III) or (IIIa) may be administered to patients for PET imaging in amounts sufficient to yield the desired signal, typical radionuclide dosages of 0.01 to 100 mCi, preferably 0.1 to 50 mCi, most preferably 1 to 20 mCi, will normally be sufficient per 70 kg bodyweight.

The radiolabelled conjugates of formula (III) or (IIIa) may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Viewed from a further aspect the invention provides the use of a radiolabelled conjugate of formula (III) or (IIIa) or a salt thereof as defined above for the manufacture of a radiopharmaceutical for use in a method of in vivo imaging, suitably PET, and preferably for imaging of a disease or condition associated with angiogenesis; involving administration of said radiopharmaceutical to a human or animal body and generation of an image of at least part of said body.

Viewed from a still further aspect the invention provides a method for in vivo diagnosis or imaging of a disease or condition associated with angiogenesis involving administering a radiopharmaceutical to said body, e.g. into the vascular system and generating an image of at least a part of said body to which said radiopharmaceutical has distributed using PET, wherein said radiopharmaceutical comprises a radiolabelled conjugate of formula (III) or (IIIa) or a salt thereof.

Viewed from a further aspect the invention provides a method of monitoring the effect of treatment of a human or animal body with a drug to combat a condition associated with cancer, preferably angiogenesis, e.g. a cytotoxic agent, said method comprising administering to said body a radiolabelled conjugate of formula (III) or (IIIa) or a salt thereof and detecting the uptake of said conjugate by cell receptors, preferably endothelial cell receptors and in particular $\alpha v \beta 3$ receptors, said administration and detection optionally but preferably being effected repeatedly, e.g. before, during and after treatment with said drug.

In yet another embodiment of the instant invention, there is provided a kit for the preparation of a radiofluorinated tracer comprising a prosthetic group of formula (II) and a compound of formula (I).

In use of the kits, the compound of formula (II) would be added to the compound of formula (I) respectively which may suitably be dissolved in aqueous buffer (pH 1-11). After reaction at a non-extreme temperature for 1 to 70 minutes, the labelled peptide may be purified, for example, by solid-phase extraction (SPE) or high performance liquid chromatography (HPLC) and collected.

EXAMPLES

The invention is illustrated by way of examples in which the following abbreviations are used:

HPLC: high performance liquid chromatography

NMR: nuclear magnetic resonance

TFA: trifluoroacetic acid.

hr(s): hour(s)

min(s): minute(s)

DMAP: 4-(dimethylamino)pyridine

THF: tetrahydrofuran

DCM: dichloromethane

DMF: N,N-dimethylformamide

TBAF: tetrabutylammonium fluoride

MeOH: methanol

TLC: thin layer chromatography

TIS: triisopropylsilane

DMSO: dimethylsulphoxide

PBS: phosphate buffered saline

PyAOP: [7-azabenzotriazol-1-yloxytris(pyrrolidino)phosphonium-hexafluorophosphate]

Boc: t-butoxycarbonyl

RT: room temperature

Example 1
Preparation of 4-trimethylammonium benzaldehyde triflate (Compound 1)

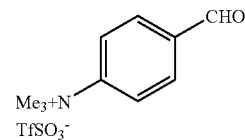

This compound was synthesised according to the procedure described by Haka et al (J. Labelled Cpds.& Radiopharms 1989 27(7) 823).

Example 2

Preparation of Peptide Precursor (Compound 3)

The peptide, Compound 2 was synthesised using standard peptide synthesis.

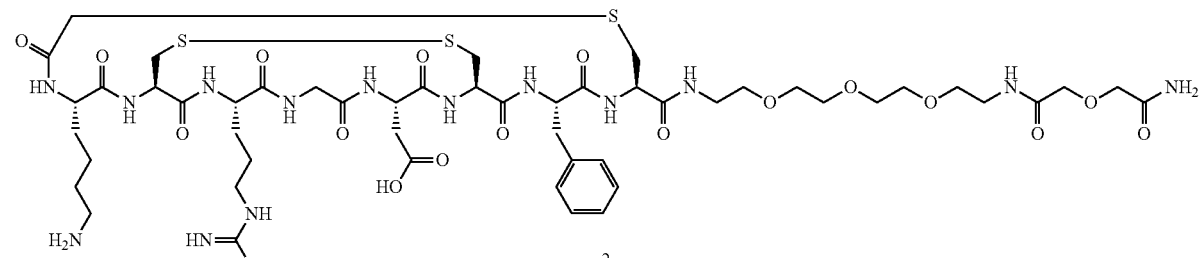

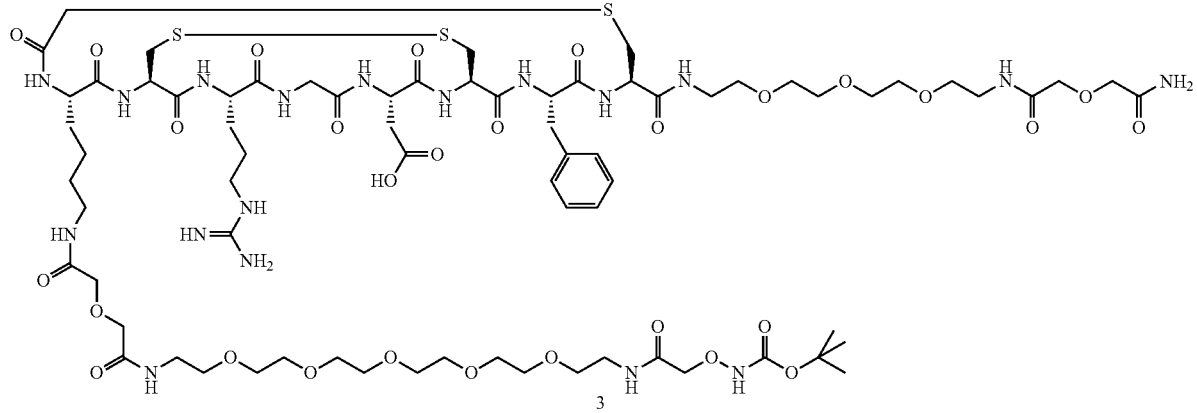

(a) 1,17-Diazido-3,6,9,12,15-pentaoxaheptadecane

A solution of dry hexaethylene glycol (25 g, 88 mmol) and methanesulphonyl chloride (22.3 g, 195 mmol) in dry THF (125 mL) was kept under argon and cooled to 0° C. in an ice/water bath. A solution of triethylamine (19.7 g, 195 mmol) in dry THF (25 mL) was added dropwise over 45 min. After 1 hr the cooling bath was removed and the reaction was stirred for another for 4 hrs. Water (55 mL) was then added to the mixture, followed by sodium hydrogencarbonate (5.3 g, to pH 8) and sodium azide (12.7 g, 195 mmol). THF was removed by distillation and the aqueous solution was refluxed for 24 h (two layers were formed). The mixture was cooled, ether (100 mL) was added and the aqueous phase was saturated with sodium chloride. The phases were separated and the aqueous phase was extracted with ether (4×50 mL). The combined organic phases were washed with brine (2×50 mL) and dried (MgSO$_4$). Filtration and evaporation of the solvent gave 26 g (89%) of a yellow oil. The product was used in the next step without further purification.

(b) 17-Azido-3,6,9,12,15-pentaoxaheptadecanamine

To a vigorously stirred suspension of 1,17-diazido-3,6,9,12,15-pentaoxaheptadecane (25 g, 75 mmol) in 5% HCl (200 mL) was added a solution of triphenylphosphine (19.2 g, 73 mmol) in ether (150 mL) over 3 hrs at room temperature. The reaction mixture was stirred for additional 24 hrs. The phases were separated and the aqueous phase was extracted with dichloromethane (3×40 mL). The aqueous phase was cooled in an ice/water bath and the pH was adjusted to 12 by addition of solid potassium hydroxide. The aqueous phase was concentrated and the product was taken up in dichloromethane (150 mL). The organic phase was dried (Na$_2$SO$_4$) and concentrated giving of 22 g (95%) of a yellow oil. The product was identified by electrospray mass spectrometry (ESI-MS) (MH$^+$ calculated: 307.19; found 307.4). The crude oil was used in the nest step without further purification.

(c) 23-Azido-5-oxo-6-aza-3,9,12,15,18,21-hexaoxatricosanoic acid

To a solution of 17-azido-3,6,9,12,15-pentaoxaheptadecanamine (15 g, 50 mmol) in dichloromethane (100 mL) was added diglycolic anhydride (Acros, 6.4 g, 55 mmol). The reaction mixture was stirred overnight. The reaction was monitored by ESI-MS analysis, and more reagents were added to drive the reaction to completion. The solution was concentrated to give a yellow residue which was dissolved in water (250 mL). The product was isolated from the aqueous phase by continuous extraction with dichloromethane over night. Drying and evaporation of the solvent gave a yield of 18 g (85%). The product was characterized by ESI-MS analysis (MH$^+$ calculated: 423.20; found 423.4). The product was used in the next step without further purification.

(d) 23-Amino-5-oxo-6-aza-3,9,12,15,18,21-hexaoxatricosanoic acid

23-Azido-5-oxo-6-aza-3,9,12,15,18,21-hexaoxatricosanoic acid (9.0 g, 21 mmol) was dissolved in water (50 mL) and reduced using H$_2$(g)-Pd/C (10%). The reaction was run until ESI-MS analysis showed complete conversion to the desired product (MH$^+$ calculated: 397.2; found 397.6). The crude product was used in the next step without further purification.

(e) (Boc-aminooxy)acetyl-PEG(6)-diglycolic acid

A solution of dicyclohexycarbodiimide (515 mg, 2.50 mmol) in dioxan (2.5 mL) was added dropwise to a solution of (Boc-aminooxy)acetic acid (477 mg, 2.50 mmol) and N-hydroxysuccinimide (287 mg, 2.50 mmol) in dioxan (2.5 mL). The reaction was stirred at RT for 1 h and filtered. The filtrate was transferred to a reaction vessel containing a solution of 23-amino-5-oxo-6-aza-3,9,12,15,18,21-hexaoxatricosanoic acid (1.0 g, 2.5 mmol) and N-methymorpholine (278 µl, 2.50 mmol) in water (5 mL). The mixture was stirred at RT for 30 min. ESI-MS analysis showed complete conversion to the desired product (MH$^+$ calculated: 570.28; found 570.6).

The crude product was purified by preparative HPLC (column: Phenomenex Luna 5µ C18 (2) 250×21.20 mm, detection: 214 nm, gradient: 0-50% B over 60 min where A=H$_2$O/0.1% TFA and B=acetonitrile/0.1% TFA, flow rate: 10 mL/min) affording 500 mg (38%) of pure product.

The product was analyzed by HPLC (column: Phenomenex Luna 3µ C18 (2), 50×2.00 mm, detection: 214 nm, gradient: 0-50% B over 10 min where A=H$_2$O/0.1% TFA and B=acetonitrile/0.1% TFA, flow rate: 0.75 mL/min, Rt=5.52 min). Further confirmation was carried out by NMR analysis.

(f) Conjugation of (Boc-aminooxy)acetyl-PEG(6)-diglycolic acid to Compound 2

(Boc-aminooxy)acetyl-PEG(6)-diglycolic acid (0.15 mmol, 85 mg) and PyAOP (0.13 mmol, 68 mg) were dissolved in DMF (2 mL). N-methylmorpholine (0.20 mmol, 20 μL) was added and the mixture was stirred for 10 min. A solution of Compound 2 (0.100 mmol, 126 mg) and N-methylmorpholine (0.20 mmol, 20 μL) in DMF (4 mL) was added and the reaction mixture was stirred for 25 min. Additional N-methylmorpholine (0.20 mmol, 20 μL) was added and the mixture was stirred for another 15 min. DMF was evaporated in vacuo and the product was taken up in 10% acetonitrile-water and purified by preparative HPLC (column: Phenomenex Luna 5μ C18 (2) 250×21.20 mm, detection: UV 214 nm, gradient: 5-50% B over 40 min where A=$H_2O$/0.1% TFA and B=acetonitrile/0.1% TFA, flow rate: 10 mL/min,) affording 100 mg semi-pure product. A second purification step where TFA was replaced by HCOOH (gradient: 0-30% B, otherwise same conditions as above) afforded 89 mg (50%). The product was analysed by HPLC (column: Phenomenex Luna 3μ C18 (2) 50×2 mm, detection: UV 214 nm, gradient: 0-30% B over 10 min where A=$H_2O$/0.1% HCOOH and B=acetonitrile/0.1% HCOOH, flow rate: 0.3 mL/min, Rt: 10.21 min). Further product characterisation was carried out using ESI-MS ($MH_2^{2+}$ calculated: 905.4, found: 906.0).

Example 3

Chemoselective ligation of $^{18}F$-fluorobenzaldehyde to Compound 3 to give Compound 4

3×0.5 ml acetonitrile were added and evaporated. After cooling to <40° C., a solution of trimethylammonium benzaldehyde triflate (1 mg in 0.4 ml DMSO) was added. The reaction vessel was sealed and heated to 90° C. for 15 mins to effect labelling. Meanwhile, Compound 3 (6 mg) was treated with 5% water in TFA (200 μl) for 5 mins at RT. The solvents were then removed in vacuo. The deprotected peptide was redissolved in 0.1M $NH_4OAc$ buffer, pH4 (0.4 ml) and combined with 4-$^{18}F$-fluorobenzaldehyde in the reaction vessel. The reaction vessel was sealed and heated to 70° C. for 15 mins to effect conjugation. After cooling to room temperature, the product was obtained by preparative radio HPLC (column Phenomenex Luna C18(2) 5 μm 10×100 mm, solvents: A=water/0.1% TFA and B=acetonitrile/0.1% TFA; gradient 15-25% B over 5 min; 25% B for 12 mins; 25-50% B over 10 mins; flow 4.0 ml/min, UV detection at 210 and 254 nm). The product fraction was diluted with water (10 ml) and loaded onto a SepPak C18-plus cartridge (conditioned with 10 ml EtOH and 20 ml $H_2O$). Compound 4 was eluted in ethanol (1 ml). The ethanol was removed in vacuo and compound 4 was formulated in PBS.

Method 2 a) Radiosynthesis of $^{18}F$-fluorobenzaldehyde $^{18}F$-Fluoride (up to 370 MBq) is azeotropically dried in the presence of Kryptofix 222 (5 mg in 0.5 ml acetonitrile) and

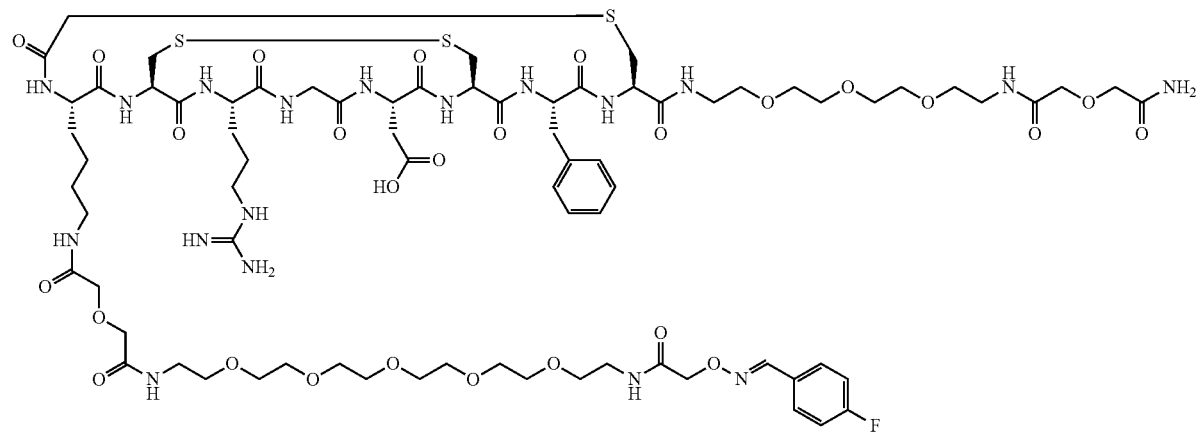

Deprotection of peptide 3 was carried out by addition of TFA containing 5% water to 10 mg of peptide. The Boc-deprotected peptide (5.9 mg, 0.0044 mmol) in 1 ml water was added to 4-fluoro benzaldehyde (Compound 1) (1.1 mg, 0.94 μl, 0.0089 mmol) in 1 ml acetonitrile. pH of the mixture was 3.5. After 45 minutes at 70 degrees the mixture was purified by reverse phase preparative chromatography twice (Phenomenex Luna C18 column, 00G-4253-N0; solvents: A=water+0.1% TFA/B=$CH_3CN$+0.1% TFA, gradient: 10-40% B over 30 min; flow 5.0 ml/minute; detected at 214 nm), affording 2.0 mg (32%) of pure compound (analytical HPLC: Phenomenex Luna C18 column, 00G-4252-E0; solvents: A=water+0.1% TFA/B=$CH_3CN$+0.1% TFA, gradient: 10-50% B over 20 min; flow 1.0 ml/minute; retention time 16.3 minutes, detected at 214 and 254 nm). Further characterisation was carried out using mass spectrometry, giving m/z value 1437.2. [M-$H^+$].

Example 4

Radiosynthesis of $^{18}F$-compound 4

Method 1

$^{18}F$-fluoride (up to 370 MBq) was azeotropically dried in the presence of Kryptofix 222 (5 mg in 0.5 ml acetonitrile) and potassium carbonate (50 μl 0.1M solution in water) by heating under $N_2$ to 110° C. for 20 mins. During this time potassium carbonate (50 μl 0.1M solution in water) by heating under $N_2$ to 110° C. for 20 mins. During this time 3×0.5 ml acetonitrile are added and evaporated. After cooling to <40° C., a solution of trimethylammonium benzaldehyde triflate (1 mg in 0.4 ml DMSO) is added. The reaction vessel is sealed and heated to 90° C. for 15 mins to effect labelling. The crude reaction mixture is cooled to room temperature and diluted by addition of water. The mixture will be passed sequentially through ion exchange cartridges (preconditioned with ethanol (or acetonitrile) and water) and eluted in an acetonitrile/water mixture. The eluate will be concentrated using a C18 Seppak, and the fluorobenzaldehyde will be eluted in acetonitrile.

b) Conjugation of Compound 3 and 4-$^{18}F$-fluorobenzaldehyde

Compound 3 is treated with 5% water in TFA for 5 mins at room temperature. The solvents are then removed by evaporation under vacuum. The peptide is redissolved in 0.1M $NH_4OAc$ buffer, pH4 (0.5 ml) and combined with 4-$^{18}F$-fluorobenzaldehyde in the reaction vessel. The reaction vessel is sealed and heated to 70° C. for 15 mins to effect conjugation. After cooling to room temperature, the product is obtained by preparative radio HPLC (as described for method 1) or by SPE.

Biological Data
Binding Studies

Using cell membrane preparations known to express the αvβ3 integrin receptor, competitive binding studies were carried out using $^{125}$I-echistatin and the F-19 labelled peptides as competing ligand. Binding curves were obtained and $K_i$'s calculated using Prism™ software.

Compound 4, had a $K_i$ value of 10 nM.

Biodistribution in Lewis Lung Tumours

Mice (male C57BL/6, ca. 25 g) were injected sub-cutaneously into the inner right thigh with Lewis lung carcinoma (LLC) cells (0.1 mL, 1×10$^7$ cells/mL in medium). Animals were monitored for tumour growth for up to 15 days, with this time selected during model development as it showed the highest level of angiogenesis.

To determine the biodistribution of $^{18}$F-compounds, tumour-bearing animals were injected with test article (0.1 mL, 5-10 MBq/mL) as an intravenous bolus via the tail vein. At various times post injection animals were euthanased. Muscle, kidneys, urine, lung, liver, stomach, small intestine, large intestine, thyroid, tumour were dissected and a blood sample taken. Dissected tissues and blood samples were weighed and counted (Wallac automatic gamma counter system). At least three animals per time point were studied. Results are expressed as % id and % id per gram of tissue.

Table 1 shows biodistribution of Compound 4 in the mouse Lewis Lung tumour model. Summarised data over time. Average data (n>3) of 5 independent experiments, presented as Mean (SD).

TABLE 1

| TIME (MINS P.I.) | BLOOD % ID/G | MUSCLE % ID/G | LUNG % ID/G | LIVER % ID/G | TUMOUR % ID/G |
|---|---|---|---|---|---|
| 5 | 6.35 (2.34) | 1.78 (0.57) | 6.54 (1.71) | 6.01 (1.03) | 2.69 (0.53) |
| 60 | 0.84 (0.39) | 0.56 (0.23) | 2.12 (0.90) | 1.48 (0.65) | 1.84 (0.45) |
| 120 | 0.45 (0.13) | 0.27 (0.07) | 1.17 (0.28) | 0.89 (0.29) | 1.49 (0.32) |

| TIME (MINS P.I.) | TUMOUR: BLOOD | TUMOUR: MUSCLE | TUMOUR: LUNG | TUMOUR: LIVER |
|---|---|---|---|---|
| 5 | 0.48 | 1.62 | 0.45 | 0.46 |
| 60 | 2.27 | 3.60 | 0.95 | 1.35 |
| 120 | 3.31 | 5.80 | 1.27 | 1.75 |

As comparison, biodistribution of Compound 5 in the mouse Lewis Lung tumour model is shown in Table 2. Summarised data over time. Average data (n>3) of 5 independent experiments, presented as Mean (SD).

TABLE 2

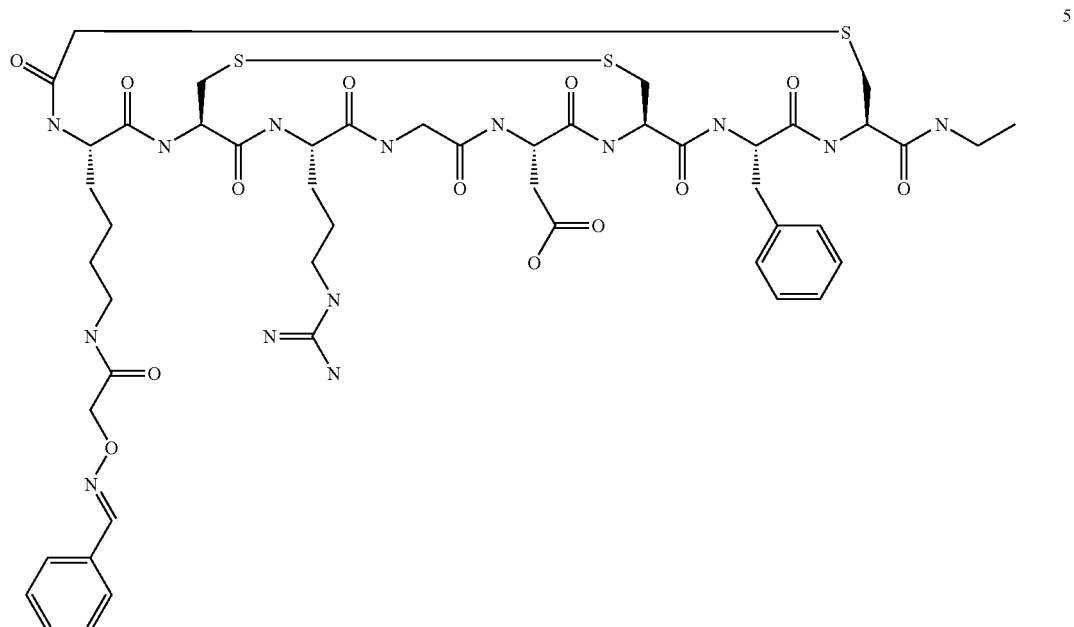

5

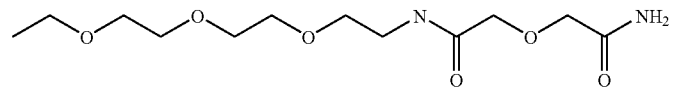

| TIME (MINS P.I.) | BLOOD % ID/G | MUSCLE % ID/G | LUNG % ID/G | LIVER % ID/G | TUMOUR % ID/G |
|---|---|---|---|---|---|
| 5 | 7.30 (1.3) | 2.27 (0.6) | 8.67 (1.4) | 7.6 (0.9) | 4.10 (0.9) |
| 60 | 0.90 (0.2) | 0.87 (0.3) | 3.37 (0.5) | 3.70 (0.9) | 2.07 (0.3) |
| 120 | 0.71 (0.2) | 0.44 (0.1) | 2.03 (0.4) | 3.28 (0.9) | 1.12 (0.3) |

TABLE 2-continued

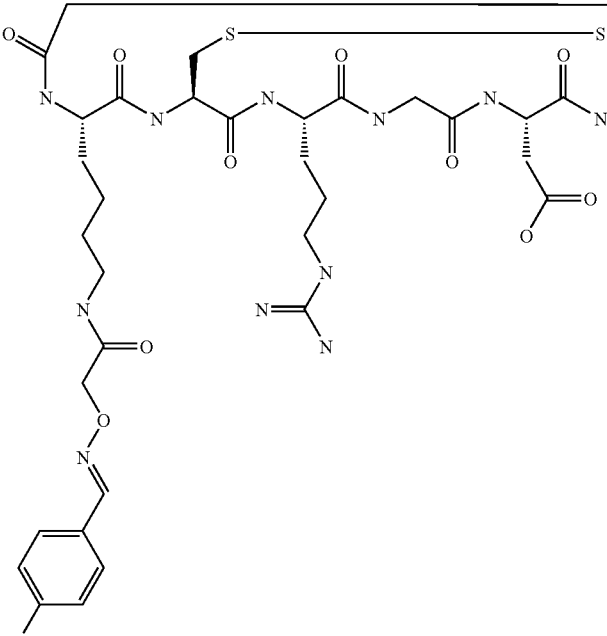

| TIME (MINS P.I.) | TUMOUR: BLOOD | TUMOUR: MUSCLE | TUMOUR: LUNG | TUMOUR: LIVER |
|---|---|---|---|---|
| 5 | 0.6 | 1.8 | 0.5 | 0.5 |
| 60 | 2.3 | 2.6 | 0.6 | 0.6 |
| 120 | 1.6 | 2.6 | 0.6 | 0.3 |

The additional PEG moiety in compound 4 imparts significantly more favourable in vivo characteristics. Specifically the remaining activity present in background tissues such as blood, muscle, lung and liver for compound 4 after 120 minutes is substantially less than for compound 5. Subsequently tumour:background ratios are significantly better thus enabling imaging.

The invention claimed is:

1. A method for radiofluorination comprising reaction of a compound of formula (I)

(I)

wherein the vector in formula (I) is of formula (A):

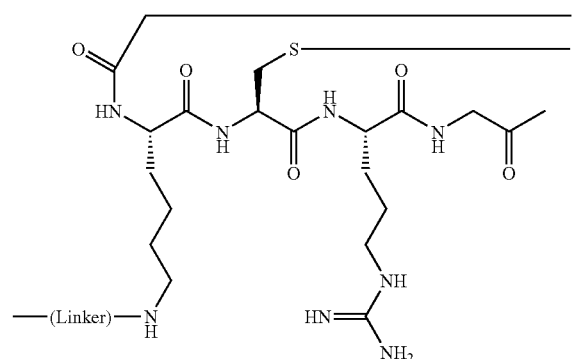

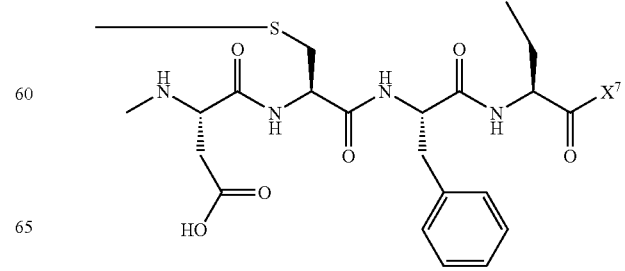

wherein $X^7$ is either —$NH_2$ or

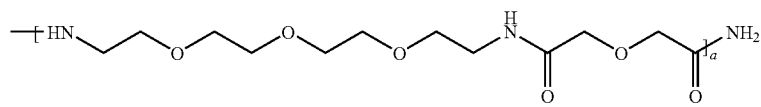

wherein a is an integer of from 1 to 10, preferably a is 1: with a compound of formula (II):

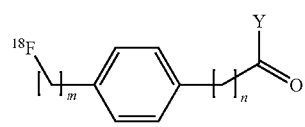

(II)

wherein:

n is an integer of 0 to 20; m is an integer of 0 to 10;

Y is hydrogen, $C_{1-6}$ alkyl, or phenyl to give a compound of formula (III)

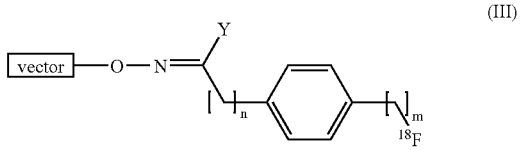

(III)

wherein m, n, and Y are defined as for the compound of formula (II) and the vector is as defined for the compound of formula (I).

2. A method according to claim 1 wherein the compound of formula (I) is of formula (Ia):

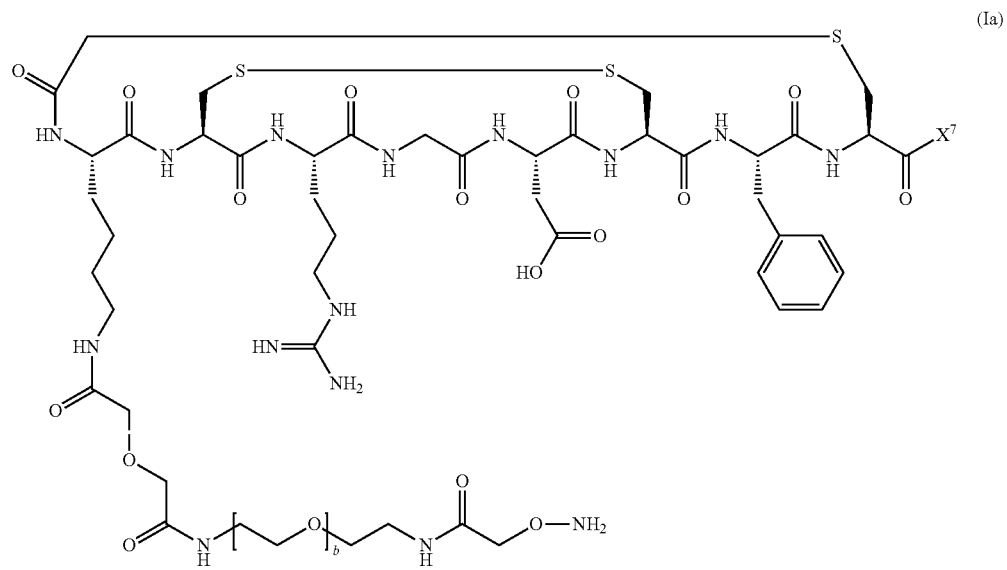

(Ia)

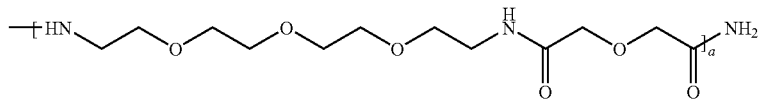

wherein a is an integer of from 1 to 10, preferably a is 1 and b is an integer of from 2 to 20 and is preferably 3 to 10, most preferably 5.

wherein $X^7$ is either —$NH_2$ or

* * * * *